United States Patent [19]

Bandyopadhyay et al.

[11] Patent Number: 5,730,986
[45] Date of Patent: Mar. 24, 1998

[54] PROCESS FOR THE ISOLATION OF AN ACTIVE PRINCIPLE FROM AZADIRACHTA INDICA USEFUL FOR CONTROLLING GASTRIC HYPERACIDITY AND GASTRIC ULCERATION

[75] Inventors: Uday Bandyopadhyay; Ratna Chatterjee; Ranajit Kumar Bandyopadhyay, all of Calcutta, India

[73] Assignee: Council of Scientific & Industrial Research, New Delhi, India

[21] Appl. No.: 596,637

[22] Filed: Feb. 5, 1996

[30] Foreign Application Priority Data

Jun. 14, 1995 [IN] India ............... 1100/DEL/95

[51] Int. Cl.$^6$ ............................................... A61K 35/78
[52] U.S. Cl. ............................................... 424/195.1
[58] Field of Search ............................... 424/195.1

[56] References Cited

U.S. PATENT DOCUMENTS

| | | | |
|---|---|---|---|
| 4,515,785 | 5/1985 | Shimizu et al. | 424/195.1 |
| 5,391,779 | 2/1995 | Lidert | 514/453 |
| 5,420,318 | 5/1995 | Lidert et al. | 554/193 |

*Primary Examiner*—Jean C. Witz
*Attorney, Agent, or Firm*—Ladas & Parry

[57] ABSTRACT

A new process for isolation of a phenolic glycoside from Neem bark aqueous extract. This phenolic glycoside is highly potent in inhibiting gastric acid secretion and stress-induced gastric ulceration. The aqueous extract is lyophilised and the powder is extracted with petroleum ether. The insoluble residue is extracted with solvents of increasing polarity and the final residue is subjected to HPLC using a reverse phase column to isolate the active compound.

14 Claims, No Drawings

PROCESS FOR THE ISOLATION OF AN ACTIVE PRINCIPLE FROM AZADIRACHTA INDICA USEFUL FOR CONTROLLING GASTRIC HYPERACIDITY AND GASTRIC ULCERATION

BACKGROUND OF THE INVENTION

This invention relates to a process for the isolation of an active principle from *Azadirachta indica* useful for controlling gastric hyperacidity and gastric ulceration.

DESCRIPTION OF THE PRIOR ART

Hyperacidity or hyperchlorhydria, a burning global problem, from which about 5% of world population is suffering today, is due to excess secretion of hydrochloric acid (HCl) from the gastric mucosa. The cause of this hypersecretion is obscure except that it is due to hyperactivity of the proton pumping $H^+-K^+$-ATPase of the parietal cell (Sachs, Penny & Lewin. Physiol. Rev. 58, 106, 1978). Hyperacidity may originate from stress and tension in our daily life. It may result from nonsteroidal and steroidal antiinflammatory drug therapy for treatment of some pathological conditions. Constant secretion of HCl also prevents mucosal wound healing and aggravates gastric ulceration, a disease caused by imbalance between some aggresive factors and cytoprotective factors of the gastric mucosa. Acid secretion is controlled by an interplay of physiological secretagogues. Histamine interacts with the $H_2$ receptor of the parietal cell and triggers acid secretion through elevation of cAMP and $Ca^{++}$ leading to the activation of $H^+-K^+$-ATPase (Sachs, Carlsson, Londberg & Wallmark. Ann. Rev. Pharmacol. Toxical. 28, 269, 1988). Acetylcholine interacts with the muscarinic receptor and stimulates HCl secretion by increasing intracellular diacylglycerol, $IP_3$ and $Ca^{++}$ (Muallem & Sachs, Amer. J. Physiol. 248, C216, 1985). Gastrin does this by transient hike of intracellular $Ca^{++}$ by interacting with the gastric receptor (Soll, Amerian, Thomas, Ready & Elashoft, J. Clin. Inv., 73, 1434, 1984). How cAMP, $Ca^{++}$ or $IP_3$, the second messengers, transmits the signal to the $H^+-K^+$-ATPase is still obscure.

The medications to combat hyperacidity and ulceration (Breenton. In Goodman's & Gilman's The Pharmacological Basis of Therapeutics, eds. Gilman, Rall, Nies & Taylor, 2, 897, 1991) are of three types: [1] $H_2$-receptor blockers which block the occupancy of the secretagogue with the receptor causing uncoupling of stimulus-secretion coupling, e.g., cimetidine, ranitidine, famotidine and nizatidine; muscarinic cholinergic receptor blockers such as atropine, pirenzepine and telenzepine; [2] Inactivator of $H^+-K^+$-ATPase, e.g. omeprazole; and [3] Different antacids (alkali gels, e.g., $Al(OH)_3$, $Mg(OH)_2$ etc.).

A variety of adverse reactions have been reported for these medications (Breenton. In Goodman's & Gilman's The Pharmacological Basis of Therapeutics. eds. Gilman, Rall, Nies & Taylor, 2, 897, 1991). Cimetidine causes altered laxation, headache, dizziness and nausea, myalgia, skin rashes and itching, incidence of symptoms related to the central nervous system (CNS), impaired renal function, loss of libido, impotence and gynecomastia (Howden & Hunt. Peptic ulcer disease. In A Pharmacological Approach to Gastrointestinal Disorders. ed. Lewis J. 3, 1994). Cimetidine also inhibits cytochrome $P_{450}$-catalyzed drug oxidation and hydroxylation of estradiol to increase the plasma concentration in men. Cimetidine occasionally causes hematological effects (various cytopenias) and alters function of immune system. Ranitidine also has several side effects (Howden & Hunt, Peptic ulcer disease, in A Pharmacological Approach to Gastrointestinal Disorders, ed. Lewis J. 3, 1994) and causes headache, mild diarrhea and a reversible form of drug-induced hepatitis in some patients. It also causes reversible mental confusion in some sick, elderly patients. Very little is known about famotidine and nizatidine as they have been marketed recently. Omeprazole causes gastrointestinal troubles including nausea, diarrhea and abdominal colic and CNS effects (e.g. headache, dizziness, somnolence). Skin rash, leucopenia and transient elevation of plasma activities of hepatic aminotransferases have been observed occasionally. Omeprazole reduces the secretion, synthesis and gene expression of pepsinogen in rat stomach (Kakel, Ichinore, Tsukada, Tatematsu, Tezuka, Yahagi, Matsushima, Miki, Kurokawa, Takahashi & Fukamachi. Biochem. Biophys. Res. Commun. 195, 997, 1993). Gastric mucosal hypertrophy and carcinoma have been reported with long term therapy of omeprazole (Ivy, Amer. J. Med. 84, Suppl.2A, 41, 1988). Antacids such as $Al(OH)_3$ causes constipation while $Mg(OH)_2$ causes loose stools or diarrhea. In a person with impaired renal function long term administration of $Al^{3+}$ initiates osteodystrophy, proximal myopathy and encephalopathy; the latter may take the form of dementia or seizures. Considering the side effects and disadvantages of these drugs, identification of a better drug having less toxicity but potent acid and ulcer inhibitory activity is urgently required to control these human sufferings. It is accepted that natural products having therapeutic value are less toxic for use as medications for humans and attempts to identify such products is always welcome.

Plants are part and parcel of human society from the dawn of civilization and extensive uses of neem (Margosa tree) for the treatment of a variety of human diseases are reminiscent of broad spectrum activities of some modern medicines. *Azadirachta indica* A. Juss (syn. Melia azadirachta) and *Melia azedarach* Linn are the two closely related species of the Meliaceae. The former is popularly known as the Indian neem or the Indian lilac and the latter as the Persian lilac. *A. indica* is an evergreen tree cultivated in various parts of India and almost every part of this plant has been used in the folk medicine in India from antiquity (Chopra, Chopra, Handa & Kapur. Indigenous drugs of India. Dhur & Sons Pvt. Ltd., Calcutta, 360, 1958). The aqueous extract of bark is regarded as tonic, astringent and useful in treating fever, vomiting and skin diseases; the leaves are beneficial in all types of anorexia and in skin diseases and the fruits are described as purgative and emollient and are useful in the treatment of intestinal worms, urinary diseases and piles (Chatterjee & Pakrashi. The treatise on Indian Medicinal Plants. eds. Chatterjee & Pakrashi, 3, 76, 1994). The water soluble fraction of the alcoholic extract of the green leaves has been found to possess significant hypoglycemic properties (Murty, Rao, Rao & Murty. Ind. J. Pharmacol. 10, 247, 1978; Pillai & Shantakumari. Ind. J. Med. Res. 74, 931, 1981). The aqueous extract of neem leaves possess gastric antiulcer activity (Garg, Nigam & Ogle. Planta Med. 59, 215, 1993).

The juice of the leaves of *M. azadarach* is said to be anthelmentic and emmenagogue. The root is useful in the treatment of tumors (Japanese Patent. Terumo Corporation, 2.522.001, 1983, C.A. 10000 168227), pain in the heart, leucoderma and blood impurities. The leaves and bark are used internally and externally in leprosy and scrofula, in the treatment of eczema and relief of asthmatic attacks.

Azadirachtin, an oxygenated complex tetranotriterpenoid isolated from neem fruit ethanol extract, is widely used as a pesticide having phagorepellent, antifeadent and systemic growth disruptor properties in insects (Butterworth, Morgan & Percy. J. Chem. Soc. Perkin. Trans. 1, 2445, 1972; Gill & Lewis, Nature, 236, 159, 1972; Zanno, Miura, Nakanishi & Editor. J. Amer. Chem. Soc. 97, 1975, 1975; Aldhons. Science, 258, 893, 1992; Govindachari, Current Sci. 63, 117, 1992; Grossman & Ley, Tetrahedron, 50, 11553, 1994). Azadirachtin has recently been shown to be active against larva of P. xylostella L (Verkerk & Wright, Pest. Sci. 37, 83, 1993) and inhibitory to the development of malarial parasites (Jones, Delholm, Ley, Lovell, Wood & Sinden. FEM Microb. Letts. 120, 267, 1994). Neem oil also possesses anti-fertility property (Juneja & Williams. Pharmacol. Letts. Life Sc. 53, 279, 1993; Upadhyay, Dhawan, Sharma & Talwar. Contraception, 49, 161, 1994; Kaushic & Upadhyay, Contraception, 51, 203, 1995). Spermicidal, diuretic and anti-inflammatory effects of neem are also reported (Sharma & Saxena. Ind. J. Med. Res 13, 1038, 1959; Shah, Sheth., Vide & Shah. Ind. J. Med. Res. 12, 150, 1958; Pillai & Santakumari. Planta Med. 43, 59, 1981). Nimbidin, the bitter principle of neem, has been shown to have antigastric ulcer activity (Pillai, Suganthan, Seshadri & Santakumari. Ind. J. Med. Res. 68, 169, 1978). In fact neem has become cynosure of world wide research effort today for its beneficial use in present day civilization. More than 100 different compounds have been isolated and characterized from neem (Chatterjee & Pakrashi. The treatise on Indian Medicinal Plants, 3, 76, 1994).

DETAILED DESCRIPTION OF THE INVENTION

The main object of the present invention is to provide a process for the isolation or an active principle from the plant *Azadirachta indica* which is useful for controlling gastric hyperacidity and gastric ulceration. Accordingly, the present invention provides a process for the isolation of an active principle which is a phenolic glycoside from *Azadiracha indica* (neem) useful in the treatment of gastric hyperacidity and gastric ulceration, which comprises:

[a] Preparing an aqueous extract from different parts of *Azadiracha indica* (neem) by conventional methods and separating undissolved impurities by known methods;

[b] Lyophilizing the said extract obtained in step [a] by conventional methods to form powder;

[c] Extracting the lyophilised powder with solvents with increasing polarity selected from;
   (i) petroleum ether, ethyl acetate, methanol, butanol;
   (ii) petroleum ether, butanol, ethanol and acetone;
   (iii) petroleum ether, chloroform, butanol and methanol;
   (iv) petroleum ether, dichloroethane, 2-propanol and methanol.

[d] Subjecting the residue obtained in step [c] to HPLC on a reverse-phase column capable of separating molecules having different hydrophobicities.

[e] Separating the fraction coming out of the column which has a maximum absorbtion of UV at 280 nm containing the phenolic glycoside.

[f] Lyophilizing the eluate obtained in step [e] to form a powder of the phenolic glycoside.

In a preferred embodiment of the invention the aqueous extraction of small pieces of the parts of neem plants such as leaves, flowers, bark is effected using distilled water of pH ranging from 5.5-7.0. The soaking of the pieces may be effected for a period of 3-48 hrs at ambient temperature.

The lyophilization of the extract to form a powder is effected by freeze drying.

The HPLC column used is a reverse-phase. $C_{18}$ column like u Bondapak, Novapak or Deltapak. The residue in step [d] is subjected to HPLC at a flow rate ranging from 0.5 ml/min–3 ml/min for collecting the eluate in the period in the range of 6 min–60 min. The phenolic glycosides coming out of the column are detected from their maximum absorbance at 280 nm which shifts to 293 nm by addition of alkali and gives positive Molisch's test for carbohydrate.

Different parts of the *Azadirachta indica* (neem) such as leaves, flowers, and bark are soaked in water in a conical flask. The bark of plant is preferred. The flask is shaken occasionally. The pH of the solution may be maintained between 5.5–7.0 by the addition of HCl or bicarbonate whichever is required. The water extract is filtered and then lyophilized by freeze drying. The lyophilized powder is first extracted with solvents with increasing polarity. The solvent systems which can be used for the purpose may be any one of the followig:

(i) petroleum ether, ethyl acetate, methanol and butanol,
(ii) petroleum ether, butanol, ethanol, and acetone;
(iii) petroleum ether, chloroform, butanol, and methanol;
(iv) petroleum ether, dichloroethane, 2-propanol and methanol.

The residue obtained after extracting with the highest polar solvent is subjected to HPLC using reverse-phase column capable of separating molecules based on hydrophobicity. The fractions from the column containing the phenolic glycoside having maximum absorption at 280 nm is taken and lyophilized.

ISOLATION OF THE ACTIVE PRINCIPLE

Extraction and preparation of test samples:

The following examples are given by way of illustration of the process of the present invention and should not be construed to limit the scope of the present invention.

EXAMPLE 1

100 gm of bark of *Azadirachta indica* in small fine pieces and air dried in the shade was soaked in 1,000 ml of glass distilled water for 30 hr in a three liter conical flask at room temperature (20°–30° C.). The flask was shaken occasionally. The water extract, brown red in color, was filtered through Whatman No. 1 and then lyophilized. The lyophilized powder (3 gm) was first extracted with 100 ml petroleum ether (b.p. 60°–80° C.). The petroleum ether extract was discarded. The residue was subsequently extracted with 100 ml ethylacetate. The ethylacetate insoluble part was then extracted with 150 ml methanol and finally the methanol insoluble part was extracted with 100 ml n-butanol. The methanol soluble part showed some activity. n-Butanol insoluble part showed acid inhibitory and antiulcer activity in both in vivo and in vitro experiments. The n-butanol insoluble part was further resolved in HPLC using preparative $C_{18}$ deltapak column and eluted with 50:50=methanol:water at a flow rate of 1.5 ml/min. When scanned at 280 nm, n-butanol insoluble part (which is soluble in water or in 50:50 water:methanol) was resolved into six peaks with retention time of 24 min, 34 min, 35 min, 35.5 min, 38.5 min, and 40 min and were designated as peak 1, peak 2, peak 3, peak 4, peak 5 and peak 6 respectively. Peak 1 showed the acid inhibitory activity. Homogeneity of peak 1 was tested in refractive index detector and also in 2D-TLC (solvent, ethylacetate:methylethylketone:formic acid:water=4:3:1:2 or in methanol:water=95:5). Homogeneity of peak 1 was further confirmed using $C_{18}$ ion-pair column equipped with electrochemical detector. Peak 1 was lyophilized to obtain a brown powder which is a phenolic glycoside and stored at 4° C. The yield of the active principle is 7%.

EXAMPLE 2

90 gm of the airdried bark in small pieces was soaked in 1,500 ml of glass distilled water (pH=6.2–6.5) for 35 hr in a three liter conical flask at room temperature (25°–35° C.). The flask was continuously shaken in a shaker bath. The water extract, brown in color, was filtered through Whatman No. 1 filter paper and then lyophilized. The lyophilized powder (3.5 gm) was first extracted with 150 ml petroleum ether (b.p. 60°–80° C.). The petroleum ether extract was discarded. The residue was subsequently extracted with 100 ml ethylacetate. The ethylacetate insoluble part was then extracted with 150 ml ethanol and finally ethanol insoluble part was extracted with 100 ml propanol. Ethanol soluble part showed some biological activity. Propanol insoluble part showed acid inhibitory, antisecretory and antiulcer activity in both in vivo and in vitro experiments. The propanol insoluble part was further resolved in HPLC using preparative $C_{18}$ deltapak column and eluted with 50:50= ethanol:water at a flow rate of 1.5 ml/min. When scanned at 280 nm, propanol insoluble part was resolved into six peaks with retention time of 24 min, 34 min, 35 min, 35.5 min, 38.5 min and 40 min and were designated as peak 1, peak 2, peak 3, peak 4, peak 5, and peak 6 respectively. Peak 1 showed the acid inhibitory activity. Homogeneity of peak 1 was tested in refractive index detector and also in 2D-TLC (solvent, ethylacetate:methylethylketone:formic acid:water=4:3:1:2, or in methanol:water=95:5). Homogeneity of peak 1 was further confirmed using $C_{18}$ ion-pair column equipped with electrochemical detector. Peak 1 was stored (as lyophilized powder) after removal of ethanol and water in a rotavapour to obtain a powder which is a phenolic glycoside. Yield of this active principle is 5%.

EXAMPLE 3

100 gm of air dried leaves were crushed and soaked in 1,000 ml of glass distilled water (pH 6.2–6) for 48 hrs in a three liter conical flask at room temperature (25° C.). The flask was continuously shaken and the aqueous extract was filtered through glasswool and then lyophilized. This extract is biologically active in inhibiting acid secretion and gastric ulceration. The lyophilized powder (1 gm) was first extracted with 50 ml petroleum ether (b.p. 60°–80° C.) and the petroleum ether extract was discarded. The residue was subsequently extracted with 50 ml of ethylacetate. The ethylacetate insoluble part was then extracted with 100 ml methanol and finally methanol insoluble part was extracted with 50 ml n-butanol. n-Butanol insoluble part showed acid inhibitory, antisecretory and antiulcer activity in both in vivo and in vitro experiments. n-Butanol insoluble part was further resolved in HPLC using a preparative $C_{18}$ column and eluted with 60:40=methanol:water at a flow rate of 1.0 ml/min. When scanned at 280 nm, n-butanol insoluble material resolved into four peaks with retention time of 36 min, 46 min, 47 min and 48 min and were designated as peak 1, peak 2, peak 3 and peak 4 respectively. Peak 1 showed acid inhibitory activity. Homogeneity of peak 1 was tested as done in Examples 1 and 2. Peak 1 was lyophilized to obtain a brown powder which is a phenolic glycoside. The yield of the active principle is 2%.

The active principle isolated according to the process of the present invention has been identified as a phenolic glycoside and has the following properties:

Physical:
1. The lyophilized powder is brick-red in color, readily soluble in water at a concentration up to 60 mg/ml and in DMSO at 50 mg/ml.
2. In UV spectrometry, the aqueous solution gives symmetrical peak at 224 nm and 276 nm. When a drop of concentrated KOH is added, only 276 nm peak is shifted to 298 nm and the original brick red color turned into deep red. The original color reappears on addition of acetic acid. This character is shown by standard phenolic compound.
3. In IR spectroscopy (in KBr), this material gives peak at 3380 $cm^{-1}$, 2362 $cm^{-1}$, 2360 $cm^{-1}$, 1514 $cm^{-1}$, 1512 $cm^{-1}$, 1452 $cm^{-1}$, 1382 $cm^{-1}$ and 1067 $cm^{-1}$. Some of the absorptions are due to hydroxyl group.
4. Melting point is above 260° C.
5. Optical rotation of this material is, $[alpha]^{25}+14°$ (C. 1.0, $H_2O$).
6. $^1H$ NMR of this material indicates peaks at 8.01, 7.87, 5.93, 4.69, 4.59, 4.50, 4.30, 3.94, 3.88, 3.69, 2.30, 2.19, 2.14, 2.01, 1.91, 1.80, 1.55, 1.16, 1.12, 0.8, 0.32, 0.26 and 0.15 PPM in $D_2O$ in 200 MHz/52 MM NMR spectrometer.
7. $^1H$ NMR of the isolated aglycan part of this material in DMSO using 200 MHz/52 MM NMR spectrometer shows peaks at 8.28, 3.42, 3.39, 3.15, 2.81 and 2.49 PPM.

Chemical:
1. When elemental analysis (particularly C,H,N) was carried out in CHN analyser, it gives 44.76% carbon and 4.72% hydrogen but no nitrogen.
2. It gives blue coloration with Folin Ciocalteau reagent which is positive for phenolic group. No peptide was detected in polyacrylamide gel electrophoresis.
3. Molisch's test for carbohydrate is positive. When hydrolized, the glycan part consists of arabinose, glucose, mannose, rhamnose and galactose in the ratio of 1:1:1:1:2 as detected by automated gas-liquid chromatography. By controlled digestion overnight at 28±1° C. with 5% $H_2SO_4$, an aglycan part is precipitated which is insoluble in water but readily soluble in methanol. This aglycan part is phenolic in nature as revealed by (1) its UV absorption at 279 nm which shifts to 293 nm by dilute alkali, and (2) its reduction of ferric ferricyanide to form a prussian blue color of ferric ferrocyanide—a positive test for phenolic compound.
4. Magnetometer data indicates that it lacks any transition metal ion. Other metal ions, e.g. $Na^+$, $K^+$, $Ca^{++}$ etc. are also absent as evidenced from negative flame test. Further studies to determine the exact structure of this novel compound is in progress.

The compound obtained by the process of the present invention was subjected to bioassay studies:

Animal:

Albino rats (Wistar strain of either sex, 180–200 gm) were deprived of food but allowed free access to water 24 hr before the start of the experiment and kept in cages with meshed aluminium base to avoid caprophagy.

In vivo studies:

A. Pylorus ligation-induced gastric acid secretion:

Pyloric ligation was done under light ether anaesthesia (Shay, Komarov, Fels, Meranze, Gruenstein & Siplet, Gastroenterology, 5, 43, 1945) 30 min after intraperitoneal injection of different doses of active principle (0.5–2.5 mg/100 gm). They were sacrificed by decapitation 2 hr after ligation. The gastric content was collected by flushing the stomach cavity with 2 ml of 0.9% saline through the pyloric end (Bandyopadhyay, Bhattacharyya, Chatterjee & Banerjee, Biochem. J. 284, 305, 1992). It was centrifuged at 5,000 g for 10 min in a RC-5B refrigerated Sorvall centrifuge. The clear supernatant was collected, the volume recorded and HCl content was measured by autotitration in a pH meter, Radiometer, Copenhagen.

B. Mercaptomethylimidazole (MMI)-induced gastric acid secretion:

MMI-induced gastric acid secretion was measured as described previously (Bandyopadhyay, Bhattacharya, Chatterjee & Banerjee. Biochem. J. 284, 305, 1992). Rats fasted for 24 hr were injected with active principle at different doses (0.5–2.5 mg/100 gm) and then after 30 min MMI (3 mg/200 gm) or vehicle (water) was injected (IP). After 2.5 hr, the animals were killed, abdomen was opened and the gastric fluid was collected as described. This active principle dose-dependently blocks MMI-induced gastric acid secretion.

In vitro studies:

A. Measurement of accumulation of [$^{14}$C]-aminopyrine [$^{14}$CAP] in isolated gastric glands as an index of acid secretion:

Gastric glands were prepared by controlled enzymatic digestion (Berglindh & Obrink. Acta Physiol. 96, 150, 1976). Briefly, rabbit gastric mucosa was scraped and chopped finely with scissors. Digestion was performed for 25 min at 37° C. using 20 mg collagenase/50 ml incubaton medium (NaCl, 140 mM; MgSO$_4$ 7H$_2$O 1.2 mM; CaCl$_2$ 2H$_2$O 1 mM; Hepes, 10 mM; KOH, 5.4 mM; Cimetidine, 100 uM; D(+) glucose, 0.5 mg/ml; BSA, 2 mg/ml). The glands were washed three times with incubation medium and resuspended in the same medium. [$^{14}$C]-AP was added to the gland suspension in presence and absence of different secretagogue and 1 ml aliquots were removed at 0, 15, 30 and 60 min. The samples were centrifuged briefly, the supernalant was removed, the pellet was dried and dissolved in 3N KOH. Radioactivity was determined by liquid scintillation counting. AP accumulation is expressed as CPM/mg of gland (Berglindh. Acta Physiol. Scand. 96, 150, 1976).

B. Assay of H$^+$-K$^+$-ATPase activity:

Preparation of gastric vesicles enriched in H$^+$-K$^+$-ATPase:Hog gastric mucosal microsome was prepared as described (Soumarmon, Abasfado, Bonfils & Lewine. J. Biol. Chem. 255, 11682, 1980; Wolosin & Forte. J. Biol. Chem. 256, 3149, 1981). Briefly, the scrapped fundic mucosa was washed with physiological saline and homogenized in a buffer containing 250 mM sucrose, 2 mM MgCl$_2$, 1 mM EGTA and 2 mM Tris-Cl (pH 7.4). The postmitochondrial supernatant was spun at 100,000 g for 60 min to get the microsomal pellet. This was suspended in homogenizing buffer and layered over a discontinuous sucrose gradient composed of equal volume (10 ml) of 37% and 22% (w/v) sucrose solution (sucrose solutions were made with buffer containing 1 mM EGTA and 2 mM Tris-Cl). Following centrifugation for 12 hr at 81,000 g in a Beckman ultracentrifuge, the membrane band at the interface of 22% and 37% sucrose layers was collected and used as the (H$^+$-K$^+$)ATPase enriched vesicular fraction. This fraction was stored in buffer at 1 mg/ml and kept at −20° C. for several months. All steps were carried out at 4° C.

(H$^+$-K$^+$)ATPase activity was determined as described (Beil, Hackbarth & Sewing. Brit. J. Pharmacol. 88, 19, 1986). Briefly, the enzyme activity was measured in 1 ml of an incubation medium containing 2 mM MgCl$_2$, 50 mM Tris-HCl buffer (pH 7.4), 0.1 mM EGTA, 5–10 ug membrane protein with or without 7 mM KCl and 7 mM NH$_4$Cl. It was preincubated for 2 min at 37° C., the reaction was started by 20 ul of 0.1 M ATP (final concentration 2 mM) and incubated for 10 min at 37° C. After stopping the reaction by 0.1 ml of 50% cold TCA, inorganic phosphate liberated was measured as described (Staussky & Shorr. J. Biol. Chem. 202, 675, 1953). (H$^+$-K$^+$)ATPase activity was calculated from the difference in the amount of phosphate released in the medium in presence or absence of 7 mM KCl and 7 mM NH$_4$Cl. Effect of the active principle was studied at varying concentration before the addition of ATP.

This compound, isolated according to the process described in Example 1, inhibits both pylorus-ligated and mercaptomethyl-imidazole (MMI)-induced gastric acid and volume secretion in vivo dose-dependently. At a dose of 14 ug/100 gm rat, it completely blocks acid secretion. It also reduces 70% and 62% of the volume secretion in pylorus-ligated and MMI-injected animals respectively.

In in vitro gastric gland preparation, it inhibits completely both basal and secretagogue-induced acid secretion at a concentration of 3 mg/ml gland suspension. The compound isolated according to process of the present invention inhibits (H$^+$-K$^+$)ATPase activity in a concentration dependent manner. At a concentration of 2 ug/ml, it completely inhibits the (H$^+$-K$^+$)ATPase. When compared, this compound isolated according to the process of the present invention, is at least three times more potent than omeprazole.

The active principle obtained by the process described in Example 2, behaved similarly as the compound isolated according to the process described in Example 1, in inhibiting in vivo and in vitro gastric acid secretion as well as gastric ulceration. At a dose of 20 ug/100 gm rat, it blocked acid secretion completely and reduced 60% and 65% of the volume of gastric secretion in pylorus-ligated and MMI-injected animals respectively. In in vitro gastric gland preparation, it inhibited both basal and secretagogue-induced acid secretion at a concentration of 4 mg/ml gland suspension. It also completely inhibited (H$^+$-K$^+$)ATPase activity at a concentration of 3 ug/ml.

Advantages of the present invention:

1. The phenolic glycoside isolated is useful for controlling gastric hyperacidity and gastric ulceration. This novel compound is effective at a very low concentration. No death was observed when rats were exposed to a high dose (2.0 mg/100 g rat). Thus, 14 ug/100 g rat, a dose which completely inhibits acid secretion is neither lethal nor toxic.

2. IC$_{50}$ value of the novel compound is lower than omeprazole. The compound is more potent than omeprazole for complete inhibition of H$^+$-K$^+$-ATPase.

3. The yield of the compound (from the lyophilized powder) is very high (7–8%).

4. As the novel compound isolated does not affect significantly pepsinogen secretion in gastric fluid, it may be selectively used as a drug for inhibiting hyperacidity. As acid delays ulcer healing, it is beneficial in healing gastric ulcer. It also blocks stress ulcer (Das & Banerjee. Mol. Cell. Biochem. 125, 115, 1993) by 90% at a concentration of 2 mg/100 g rat.

5. The isolated novel compound is obtained by extraction with water and its phenolic glycoside character is entirely different from the compounds isolated so far from neem tree as reported earlier (Mahato, Sahu & Poddar. Science & Culture 53, Suppl.No. 5, 1987; Chatterjee & Pakrashi. The treatise on the Indian Medicinal Plants. eds. Chatterjee & Pakrashi, 3, 76, 1994).

We claim:

1. A process for the isolation of an active principle from Azadirachta indica (neem) for treatment of gastric hyperacidity and gastric ulceration which comprises:
   a. preparing an aqueous extract from parts of Azadirachta indica (neem) and separating undissolved impurities;
   b. lyophilizing the extract obtained in step a. by conventional methods] to form a powder;
   c. extracting the lyophilized powder with solvents of increasing polarity selected from the group consisting of:
      i) petroleum ether, ethylacetate, methanol, butanol;
      ii) petroleum ether, butanol, ethanol, acetone;
      iii) petroleum ether, chloroform, butanol, methanol; and
      iv) petroleum ether, dichloroethane, 2-propanol, methanol;
   d. subjecting the residue obtained in step c to HPLC on a reverse-phase column capable of separating molecules having different hydrophobicites; and
   e. separating eluant which has a maximum absorption of UV at 280 nm.

2. A process as claimed in claim 1, wherein aqueous extract of *Azadirachta indica* is prepared from the leaves, flowers, or bark, or a combination thereof of *Azadirachta indica*.

3. A process as claimed in claim 1, wherein the aqueous extract of neem is effected by soaking the parts of neem in distilled water at a pH of from 5.5–7.0.

4. A process as claimed in claim 3 wherein the soaking of the parts of neem is effected for a period in the range of 3–48 hrs at ambient temperature.

5. A process as claimed in claim 1, wherein the lyophilization of the extract to form a powder is effected by freeze drying.

6. A process as claimed in claim 1, wherein the HPLC column used is a reverse-phase $C_{18}$ column.

7. A process as claimed in claim 1, wherein in step d the residue is subjected to HPLC at a flow rate ranging from 0.5 ml/min. to 3.0 ml/min and the eluate is collected from the column during the period in the range of 6 min–60 min said eluate containing the phenolic glycoside.

8. An isolated phenolic glycoside prepared by the process which comprises:
   a. preparing an aqueous extract from parts of *Azadirachta indica* (neem) and separating undissolved impurities;
   b. lyophilizing the extract obtained in step a. to form a powder;
   c. extracting the powder of step b. with petroleum ether to form a petroleum ether extract and a residue;
   d. extracting the residue of step c. with solvents of increasing polarity to obtain a residue, said solvents selected from the group consisting of:
      i) ethylacetate, methanol, butanol;
      ii) butanol, ethanol, acetone;
      iii) chloroform, butanol, methanol; and
      iv) dichloroethane, 2-propanol, methanol;
   e. subjecting the residue obtained in step d. to HPLC on a reverse-phase column having different hydrophobicities, and
   f. separating eluant which has a maximum absorption of UV at 280 nm.

9. An isolated phenolic glycoside characterized by:

IR spectroscopy (in Kbr)-peaks at 3380 $cm^{-1}$, 2362 $cm^{-1}$, 2360 $cm^{-1}$, 1514 $cm^{-1}$, 1512 $cm^{-1}$, 1452 $cm^{-1}$, 1382 $cm^{-1}$ and 1067 $cm^{-1}$; melting point above 260° C.; $^1$H NMR with peaks at 8.01, 7.87, 5.93, 4.69, 4.59, 4.50, 4.30, 3.94, 3.88, 3.69, 2.30, 2.19, 2.14, 2.01, 1.91, 1.80, 1.55, 1.16, 1.12, 0.8, 0.32, 0.26 and 0.15 PPM in $D_2O$ in 200 MHz/52 MM NMR spectrometer; and $^1$H NMR of isolated aglycan part of the phenolic glycoside in DMSO using 200 MHz/52 MM NMR spectrometer with peaks at 8.28, 3.42, 3.39, 3.15, 2.81 and 2.49 PPM.

10. The process of claim 2 wherein the aqueous extract is prepared from the bark.

11. The process according to claim 1 wherein the eluant is collected from the column during the period in the range of 6 min to 60 min.

12. The isolated phenolic glycoside of claim 8 wherein the eluant containing the phenolic glycoside is collected from the column during the period in the range of 6 min to 60 min.

13. The process according to claim 1 wherein the phenolic glycoside is collected from the column during the period in the range of 6 min to 60 min.

14. The process according to claim 1 wherein the active principle is a phenolic glycoside.

* * * * *